(12) United States Patent
Clyde et al.

(10) Patent No.: US 6,555,159 B2
(45) Date of Patent: Apr. 29, 2003

(54) COATING FOR GAS SENSORS

(75) Inventors: Eric P. Clyde, Bay City, MI (US); Richard F. Beckmeyer, Davisburg, MI (US); William J. Labarge, Bay City, MI (US); Marsha E. Nottingham, Howell, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/740,306

(22) Filed: Dec. 18, 2000

(65) Prior Publication Data

US 2002/0102347 A1 Aug. 1, 2002

(51) Int. Cl.⁷ ................................................. B05D 5/12
(52) U.S. Cl. ............................... 427/126.3; 427/126.4; 427/226; 427/376.2; 427/419.2
(58) Field of Search ........................ 427/226, 376.2, 427/126.3, 126.4, 419.2

(56) References Cited

U.S. PATENT DOCUMENTS

| | | |
|---|---|---|
| 3,811,899 A | 5/1974 | Stibbs et al. |
| 4,272,349 A | 6/1981 | Furutani et al. |
| 4,702,897 A | 10/1987 | Onal |
| 5,160,598 A | 11/1992 | Sawada et al. |
| 5,252,314 A | 10/1993 | DeGuire et al. |
| 5,271,821 A | 12/1993 | Ogasawara et al. |
| 5,326,597 A | 7/1994 | Sawada et al. ............. 427/448 |
| 5,389,589 A | 2/1995 | Kharas |
| 5,395,406 A | 3/1995 | Clavenna et al. |
| 5,395,654 A | 3/1995 | Philipp et al. |
| 5,423,973 A | 6/1995 | Friese et al. |
| 5,593,558 A | 1/1997 | Sugino et al. |
| 5,593,654 A | 1/1997 | Decker, Jr. et al. |
| 5,639,929 A | 6/1997 | Bharadwaj et al. |
| 5,762,737 A | 6/1998 | Bloink et al. |
| 5,814,285 A | 9/1998 | Kojima et al. |
| 5,837,634 A | 11/1998 | McLaughlin et al. |
| 5,846,615 A | 12/1998 | Sharma et al. |
| 5,849,165 A | 12/1998 | Kojima et al. |
| 5,894,038 A | 4/1999 | Sharma et al. |
| 6,015,517 A * | 1/2000 | Casey ........................ 264/44 |

FOREIGN PATENT DOCUMENTS

JP      1-232252     *   9/1989

* cited by examiner

Primary Examiner—Katherine A. Bareford
(74) Attorney, Agent, or Firm—Vincent A. Cichosz

(57) ABSTRACT

A method for making a sensor is disclosed. The method comprises: disposing an electrolyte between a first side of sensing electrode and a first side of reference electrode, disposing a first side of a protective layer adjacent to said a second side of said sensing electrode, applying a mixture of a metal oxide, a fugitive material, and a solvent to a second side of the protective layer, and calcining the applied mixture to form said a protective coating on the second side of the protective layer.

22 Claims, 3 Drawing Sheets

COATING FOR GAS SENSORS

TECHNICAL FIELD

The present disclosure relates to gas sensors, and particularly to sensors with a porous protective layer for protection of the sensor electrode from poisoning.

BACKGROUND

The automotive industry has used exhaust gas sensors in automotive vehicles for many years to sense the composition of exhaust gases, namely, oxygen. For example, a sensor is used to determine the exhaust gas content for alteration and optimization of the air to fuel ratio for combustion.

One type of sensor uses an ionically conductive solid electrolyte between porous electrodes. For oxygen, solid electrolyte sensors are used to measure oxygen activity differences between an unknown gas sample and a known gas sample. In the use of a sensor for automotive exhaust, the unknown gas is exhaust and the known gas, (i.e., reference gas), is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("exhaust gas electrode"), and a porous electrode exposed to a known gas' partial pressure ("reference electrode"). Sensors typically used in automotive applications use a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where

E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

In a conventional sensor, the sensor comprises a first electrode capable of sensing an exhaust gas and a second electrode capable of sensing a reference gas with an ionically conductive solid electrolyte disposed therebetween. High temperatures and materials such as silicon, lead and the like, present in engine components, can poison or otherwise damage the sensing electrode. In order to prevent poisoning/damage to the sensing electrode, a protective layer made of spinel or the like, has conventionally been applied to the sensing electrode.

The protective layer is designed to allow for the electrodes to sense the particular gas without inhibiting the performance of the sensor. A thick layer (or multiple layers) of protective coating more effectively inhibits the transmission of the poisoning materials, but at the expense of a decrease in the efficiency of the sensor. Furthermore, the protective layer itself can become clogged, inhibiting passage of exhaust gases for sensing. One conventional poison resistance technique comprises applying multiple layers of a heat resistant metal oxide to the electrode to form a protective layer. However, the multiple layers have a tendency to change the performance of the sensor and only provide limited poison protection.

Accordingly, there exists a need in the art for improved protective coatings for gas sensors.

SUMMARY

The drawbacks and disadvantages of the prior art are overcome by the coating for a gas sensor and method for making the same. The method for making a sensor comprises: disposing an electrolyte between a first side of sensing electrode and a first side of reference electrode, disposing a first side of a protective layer adjacent to said a second side of said sensing electrode, applying a mixture of a metal oxide, a fugitive material, and a solvent to a second side of the protective layer, and calcining the applied mixture to form said a protective coating on the second side of the protective layer.

BRIEF DESCRIPTION OF THE DRAWINGS

Referring now to the figures, which are meant to be exemplary, not limiting, and wherein like elements are numbered alike in several figures.

DESCRIPTION OF THE PREFERRED EMBODIMENT

A protective coating for gas sensors, in particular oxygen sensors, is formed from a composition comprising a metal oxide and a fugitive material. Although described in connection with an oxygen sensor, it is to be understood that the protective coating can be employed with any type of sensor such as a nitrogen oxide sensor, hydrogen sensor, hydrocarbon sensor, or the like. Furthermore, while oxygen is the reference gas used in the description disclosed herein, it should be understood that other gases could be employed as a reference gas.

Figure 1:
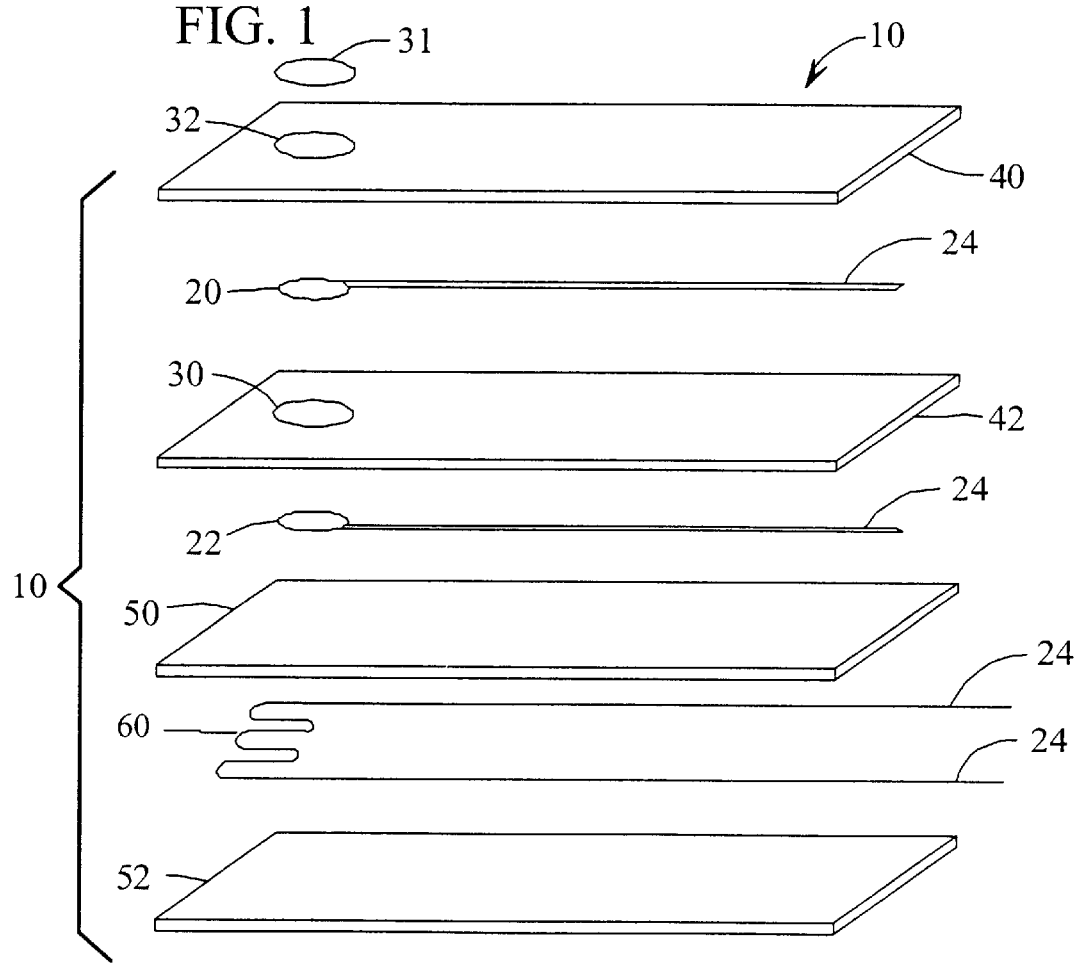
FIG. 1 is an expanded isometric view of one embodiment of an oxygen sensor.

Referring to FIG. 1, the sensor element 10 is illustrated. The exhaust gas (or outer) electrode 20 and the reference gas (or inner) electrode 22 are disposed on opposite sides of, and adjacent to, an electrolyte layer 30 creating an electrochemical cell (20/30/22). On the side of the exhaust gas electrode 20 opposite solid electrolyte 30 is an optional protective insulating layer 40 with a porous section 32 that enables fluid communication between the exhaust gas electrode 20 and the exhaust gas. A protective coating 31 can be disposed over the porous section 32. The electrolyte 30 and the porous section 32 can be disposed adjacent to, or as inserts within, layers 40, 42, respectively. Meanwhile, disposed on a side of the reference electrode 22 opposite electrolyte layer 30 is a heater 60. Typically disposed between the reference gas electrode 22 and the heater 60, as well as on a side of the heater 60 opposite the reference gas electrode 22, are one or more insulating layers 50, 52.

In addition to the above sensor components, conventional components can be employed, including but not limited to lead gettering layer(s), leads, contact pads, ground plane(s), support layer(s), additional electrochemical cell(s), and the like. The leads (24), which supply current to the heater and electrodes, are typically formed on the same layer as the heater/electrode to which they are in electrical communication and extend from the heater/electrode to the terminal end of the gas sensor where they are in electrical communication with the corresponding via (not shown) and appropriate contact pads (not shown).

Insulating layers 50, 52, and protective layer 40, provide structural integrity (e.g., protect various portions of the gas sensor from abrasion and/or vibration, and the like, and provide physical strength to the sensor), and physically separate and electrically isolate various components. The insulating layer(s), which can be formed using ceramic tape casting methods or other methods such as plasma spray deposition techniques, screen printing, stenciling and others conventionally used in the art, can each be up to about 200 microns thick or so, with a thickness of about 50 microns to about 200 microns preferred. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating and protective layers is dependent upon the specific electrolyte employed. Typically these insulating layers comprise a dielectric material such as alumina, and the like.

Disposed between the insulating layers 50, 52, is a heater 60 that is employed to maintain the sensor element at the desired operating temperature. Heater 60 can be any conventional heater capable of maintaining the sensor end at a sufficient temperature to facilitate the various electrochemical reactions therein. The heater 60, which is typically platinum, aluminum, palladium, and the like, as well as oxides, mixtures, and alloys comprising at least one of the foregoing metals, or any other conventional heater, is generally screen printed or otherwise disposed onto a substrate to a thickness of about 5 microns to about 50 microns.

Disposed on an opposite side of insulating layer 50 as heater 60 is the electrolyte 30. The electrolyte 30 can be solid or porous, can comprise the entire layer or a portion thereof, can be any material that is capable of permitting the electrochemical transfer of oxygen ions, should have an ionic/total conductivity ratio of approximately unity, and should be compatible with the environment in which the gas sensor will be utilized (e.g., up to about 1,000° C.). Possible electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing materials. For example, the electrolyte can be alumina and/or yttrium stabilized zirconia. Typically, the electrolyte, which can be formed via many conventional processes (e.g., die pressing, roll compaction, stenciling and screen printing, tape casting techniques, and the like), has a thickness of up to about 500 microns or so, with a thickness of about 25 microns to about 500 microns preferred, and a thickness of about 50 microns to about 200 microns especially preferred.

It should be noted that the electrolyte layer 30 and porous section 42 can comprise an entire layer or a portion thereof; e.g., they can form the layer (i.e., 42 and 40, respectively), be attached to the layer (porous section/electrolyte abutting dielectric material), or disposed in an opening in the layer (porous section/electrolyte can be an insert in an opening in a dielectric material layer). The latter arrangement eliminates the use of excess electrolyte and protective material, and reduces the size of gas sensor by eliminating layers. Any shape can be used for the electrolyte and porous section, with the size and geometry of the various inserts, and therefore the corresponding openings, being dependent upon the desired size and geometry of the adjacent electrodes. It is preferred that the openings, inserts, and electrodes have a substantially compatible geometry such that sufficient exhaust gas access to the electrode(s) is enabled and sufficient ionic transfer through the electrolyte is established.

The electrodes 20, 22, are disposed in ionic contact with the electrolyte layer 30. Conventional electrodes can comprise any catalyst capable of ionizing oxygen, including, but not limited to, materials such as platinum, palladium, osmium, rhodium, iridium, gold, ruthenium, zirconium, yttrium, cerium, calcium, aluminum, silicon, and the like, and oxides, mixtures, and alloys comprising at least one of the foregoing catalysts. As with the electrolyte, the electrodes 20, 22 can be formed using conventional techniques. Some possible techniques include sputtering, painting, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. Electrode leads (not shown) and vias (not shown) in the insulating and/or electrolyte layers are typically formed simultaneously with electrodes.

Following the formation of the sensing element 10, a protective coating 31 can be applied to the sensing element 10. This protective coating, which may optionally coat a portion of or all of substrate layer 40 and/or support layer 52, is formed from a composition comprising a metal oxide and a fugitive material. Possible metal oxides can include zirconia, alumina, magnesia, titania, and the like, as well as mixtures, alloys, and combinations comprising at least one of the foregoing metal oxides, with a coating comprising alpha alumina, gamma alumina, or delta alumina, as well as combinations comprising at least one of these aluminas preferred.

As used herein, "fugitive material" means a material that will occupy space until the electrode is fired, thus leaving porosity in the coating. Suitable fugitive materials are accordingly those which will release at firing temperatures, and include, but are not limited to, carbon based materials, such as carbon black, graphite, non-dissolved organics, and the like, as well as combinations comprising at least one of the foregoing materials. Preferably, carbon black is used having particle sizes of about 0.02 microns ($\mu$m) to about 0.2 $\mu$m.

The amount of metal oxide and fugitive material used to form the protective coating 31, as well as the characteristics of those materials, is based upon the desired coating characteristics. The protective coating 31 preferably has a sufficient porosity with a small enough pore size to enable the passage of exhaust gases while inhibiting passage of poisoning particulates. The porosity can be up to about 20%, with about 2% to about 15% preferred, and about 5% to about 12% especially preferred. Meanwhile, a pore size of less than about 25 microns ($\mu$m), with less than about 10 $\mu$m preferred and about 1 $\mu$m to about 2 $\mu$m is typically preferred.

As with the pore size and porosity, the thickness of the protective coating 31 is based upon the ability to filter out poisoning particulates while allowing passage of the exhaust gases to be sensed. Although a multi-layered coating can be employed, the protective coating is preferably a single layer having an overall thickness of up to or exceeding about 200 $\mu$m, with a thickness of about 120 $\mu$m to about 160 $\mu$m preferred.

Meanwhile, the composition of the unfired protective coating 31 can be up to about 98 weight percent (wt. %) first material (comprising metal oxide), with up to about 10 wt. % fugitive material; with about 93 wt. % to about 97 wt. % first material and about 3 wt. % to about 7 wt. % fugitive material preferred; and about 94 wt. % to about 96 wt. % first material and about 4 wt. % to about 6 wt. % fugitive material especially preferred; based upon the total weight of fugitive material and first material. In one embodiment, the metal oxide comprises a mixture of gamma alumina and alpha alumina. Generally, the first material comprises up to about 30 wt % gamma alumina and up to about 80 wt. % alpha alumina can be employed and optionally up to about 10 wt % aluminum nitrate; with about 25 wt. % to about 75 wt. % gamma alumina, about 25 wt. % to about 75 wt. % alpha alumina, and optionally up to about 5 wt. % aluminum nitrate preferred; with about 43.5 wt. % to about 54.5 wt. % gamma alumina, about 43.5 wt. % to about 54.5 wt. % alpha alumina, and about 1 wt. % to about 3 wt. % aluminum nitrate especially preferred. Preferably, the gamma alumina has an agglomerate size of up to about 25 $\mu$m or so, with about 6 $\mu$m to about 34 $\mu$m preferred, while the alpha alumina preferably has a particle size of up to about 1 $\mu$m, with about 0.3 $\mu$m to about 0.5 $\mu$m especially preferred.

Although the protective coating 31 can be applied to the porous protective layer in any conventional fashion using techniques such as imbibing, spraying, spray coating, painting, dipping, spin coating, vapor deposition, and the like, dipping is especially preferred. For example, a solution, suspension, ink, paste, slurry, or the like is prepared by mixing the metal oxide(s) with a sufficient amount of a fugitive material, such as carbon black, in a sufficient amount of a solvent to attain the desired viscosity mixture. Some possible solvents include water, nitric acid, benzoic acid, acetic acid, citric acid, and the like, as well as a combination comprising at least one of the foregoing solvents. Once the slurry is prepared, the slurry can then be applied to the desired area of the sensor. Typically the protective coating 31 is applied to the protective layer 32 and optionally to the substrate layer 40 and/or the support layer 52. (see FIG. 1)

Once the slurry has been applied to the sensor, it is optionally dried at temperatures up to about 100° C. for up to about 1 hour. The dried sensor is then calcined for up to about 10 hour, with less than 5 hours preferred and about 10 minutes to 60 minutes especially preferred, at a temperature sufficient to burn off the fugitive material. Preferably, calcination is completed at temperatures up to about 1,000° C., with about 500° C. to about 800° C. preferred, and with about 550° C. to about 650° C. especially preferred.

The following example is provided to further illustrate the coating for a gas sensor and is not intended to limit the scope thereof. The following example was used to prepare an exhaust sensor having a platinum electrode, yttria doped zirconia electrolyte, alumina support layers, an alumina protective layer, and a protective coating.

An electrolyte was disposed in an alumina support between two alumina supports with a platinum electrode screen printed on each support such that the electrodes were in intimate contact with the electrolyte. Electrical leads were disposed across the supports from the electrodes to contacts (vias) disposed at an end of the sensor opposite the electrodes. A protective layer, also disposed in an alumina support, was then oriented in physical contact with the sensing electrode, while the reference electrode was disposed in contact with a series of alumina support layers, with a heater disposed between the last two support layers.

A slurry was then prepared by mixing 4,900 grams (g) of gamma alumina, 4,900 g of alpha alumina, 200 g of aluminum nitrate and 490 g of carbon black with water. The sensor was dipped in the slurry and dried at 60° C. for about 10 minutes. The sensor was then calcined at 650° C. for about 1.5 hours.

Figure 2:
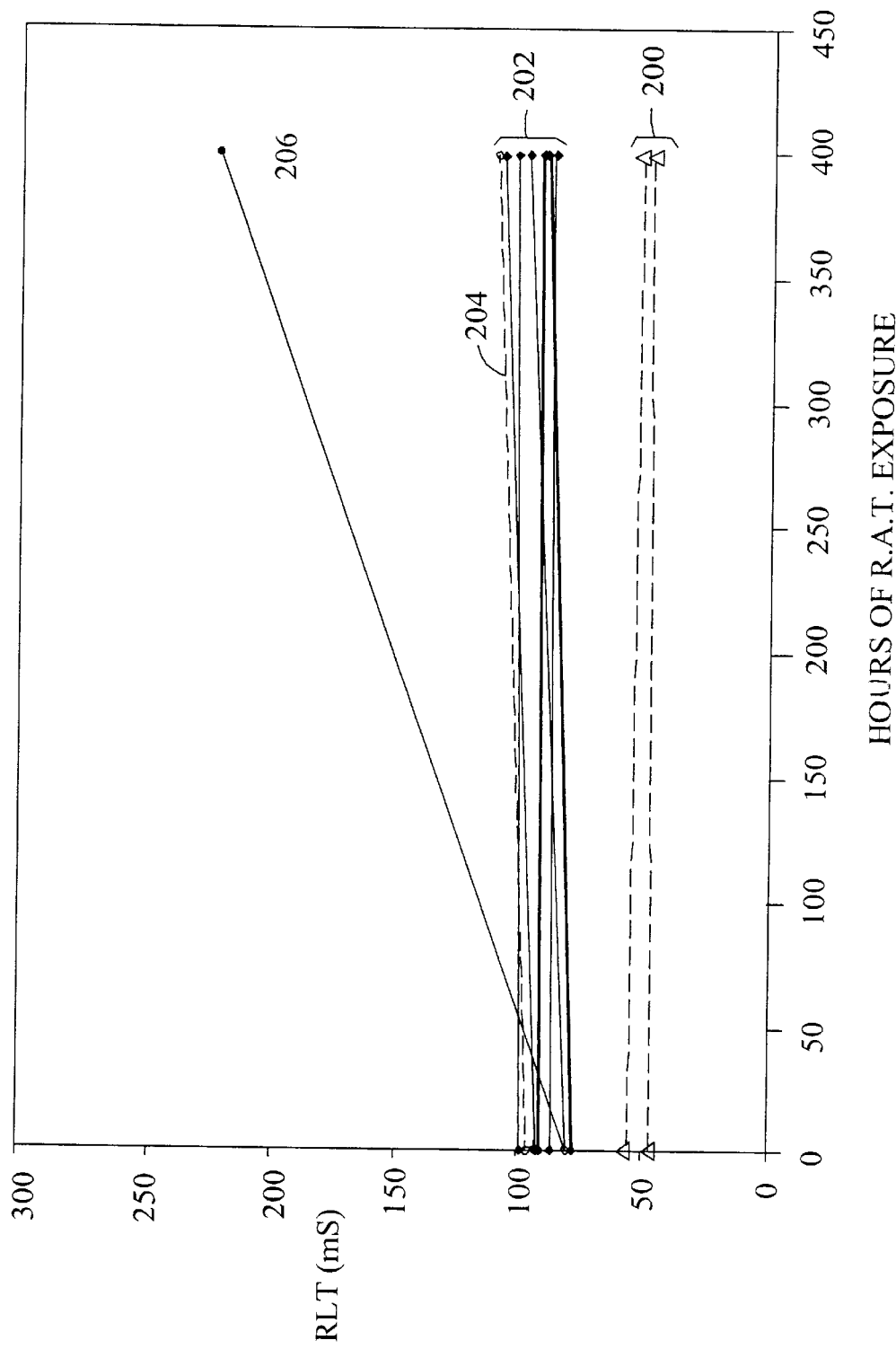
FIG. 2 is a graph showing low calcium rapid age test (RAT) durability at 260° C. for various sensors with hours of RAT exposure time on the X axis (hours) and rich to lean response time on the Y axis in milliseconds (ms).
Figure 3:
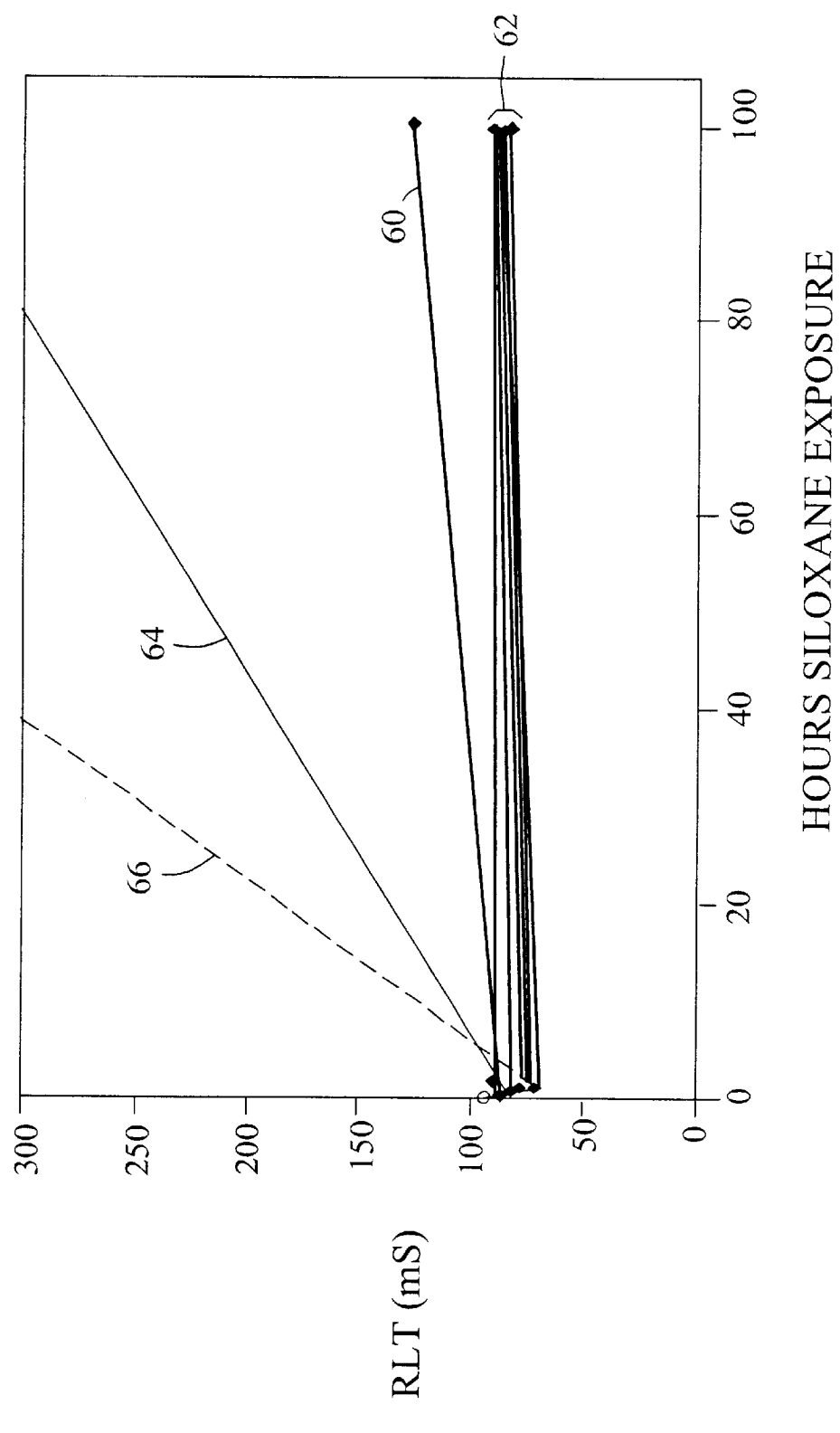
FIG. 3 is graph showing the siloxane poisoning at 400° C. with hours of siloxane exposure time on the X axis (hours) and rich to lean response time on the Y axis in ms.

FIGS. 2 and 3 graphically illustrate the low calcium rapid age and the siloxane poisoning tests, respectively. As can be seen from FIG. 2, the low density protective coating sensor maintained a rich to lean time (RLT), (under conditions of 260° C., 0.5 hertz (Hz), and an air to fuel ratio of +/−0.3 from stoichiometry) of less than about 110 milliseconds (ms) (lines 202) for 400 hours of exposure to the high temperature cycling of the RAT test.

FIG. 3 illustrates that the sensor prepared in accordance with the above example maintained a substantially better rich to lean response time for the entire 100 hours as compared to the comparative sensors also tested. Sensors prepared in accordance with the above example maintained a rich to lean response time better than about 125 milliseconds (ms) (line 60) and many of these sensors maintained a rich to lean response time better than about 90 ms (line 62) for the entire 100 hours. By comparison, the Denso (line 66) sensor with a multi-layer protective coating and the OSS (line 64) sensor had significantly longer rich to lean response times after 100 hours of siloxane exposure.

This sensor has a protective coating with lower density and demonstrates better resistance to poisoning and improved durability. The coating applied is able to resist sensor deactivation as vehicles age because of the rough texture of the coating. While smooth, flat coatings are easy to degrade due to the "glassy" zinc phosphate deposition, this coating has a superior resistance to diffusion limitation than any other coating. The sensor exhibits RLT of less than about 130 ms for over 100 hours with siloxane poisoning (1.56 ml/gal); over an order of magnitude improvement over the prior art. Additionally, a RLT of less than about 110 ms for over about 400 hours was achieved in a calcium rapid age test. It is believed that although conventional sensors fail at about 1,000 hours of actual use, this sensor will resist sensor deactivation for greater than about 2,000 hours with up to and exceeding about 4,000 hours feasible. Furthermore, the process to manufacture such a sensor does not require additional processing steps or time.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

What is claimed is:

1. A method for making a sensor, comprising:
   disposing an electrolyte between a first side of sensing electrode and a first side of reference electrode, wherein said sensing electrode has a first electrical lead in electrical communication with said sensing electrode, and wherein said reference electrode has a second electrical lead in electrical communication with said reference electrode
   disposing a first side of a protective layer adjacent to a second side of said sensing electrode;
   applying a mixture of a metal oxide, a solvent, and a fugitive material selected from the group consisting of carbon black, graphite, non-dissolved organics and combinations comprising at least one of the foregoing materials, to a second side of said protective layer; and
   calcining said applied mixture to form a protective coating on said second side of said protective layer;
   wherein said protective coating has a thickness of greater than about 120 $\mu$m.

2. The method of claim 1, wherein the mixture comprises at least 94 wt. % metal oxide and at least 3 wt. % fugitive material based upon the total weight of the fugitive material and the metal oxide.

3. The method of claim 2, wherein the mixture comprises about 93 wt. % to about 97 wt. % metal oxide and about 3 wt. % to about 7 wt. % fugitive material based upon the total weight of said fugitive material and said metal oxide.

4. The method of claim 2, wherein the mixture comprises about 94 wt. % to about 96 wt. % metal oxide and about 4 wt. % to about 6 wt. % fugitive material based upon the total weight of said fugitive material and said metal oxide.

5. The method of claim 1, wherein said protective coating has a thickness of about 120 $\mu$m to about 200 $\mu$m.

6. The method of claim 1, wherein said sensor is calcined at a temperature of at least 500° C. for at least 10 minutes.

7. The method of claim 6, wherein said sensor is calcined at a temperature of about 500° C. to about 800° C. for about 10 minutes to about 60 minutes.

8. The method of claim 6, wherein said sensor is calcined at a temperature of about 550° C. to about 650° C. for about 10 minutes to about 60 minutes.

9. The method of claim 1, wherein said fugitive material includes said carbon black, and said carbon black has particle sizes of about 0.02 $\mu$m to about 0.2 $\mu$m.

10. The method of claim 1, wherein said protective coating has a porosity of about 2% to about 15%.

11. The method of claim 1, wherein said metal oxide is selected from the group consisting of alpha alumina, gamma alumina, delta alumina, and combinations comprising at least one of the foregoing metal oxides.

12. The method of claim 1, further comprising burning off said fugitive material.

13. The method of claim 1, wherein the mixture comprises about 93 wt. % to about 98 wt % metal oxide and about 2 wt. % to about 7 wt % fugitive material based upon the total weight of the fugitive material and the metal oxide.

14. A method for making a sensor, comprising:
   disposing an electrolyte between a first side of sensing electrode and a first side of reference electrode, wherein said sensing electrode has a first electrical lead in electrical communication with said sensing electrode, and wherein said reference electrode has a second electrical lead in electrical communication with said reference electrode;
   disposing a first side of a protective layer adjacent to a second side of said sensing electrode;
   applying a mixture of a metal oxide, a solvent, and a fugitive material selected from the group consisting of carbon black, graphite, non-dissolved organics and combinations comprising at least one of the foregoing materials, to a second side of said protective layer; and
   calcining said applied mixture to form a protective coating on said second side of said protective layer;
   wherein said protective coating has a thickness of about 120 $\mu$m to about 160 $\mu$m.

15. A method for making a sensor, comprising:
   disposing an electrolyte between a first side of sensing electrode and a first side of reference electrode, wherein said sensing electrode has a first electrical lead in electrical communication with said sensing electrode, and wherein said reference electrode has a second electrical lead in electrical communication with said reference electrode;
   disposing a first side of a protective layer adjacent to a second side of said sensing electrode.
   applying a mixture of a metal oxide, a fugitive material, and a solvent to a second side of said protective layer; and
   calcining said applied mixture to form a protective coating on said second side of said protective layer, wherein said protective coating has a thickness of about 120 to about 160 micrometers.

16. A method for making a sensor, comprising:
   disposing an electrolyte between a first side of sensing electrode and a first side of reference electrode, wherein said sensing electrode has a first electrical lead in electrical communication with said sensing electrode, and wherein said reference electrode has a second electrical lead in electrical communication with said reference electrode;
   disposing a first side of a protective layer adjacent to a second side of said sensing electrode;
   applying a mixture of a metal oxide, a solvent, and a fugitive material selected from the group consisting of carbon black, graphite, non-dissolved organics and combinations comprising at least one of the foregoing materials, to a second side of said protective layer; and
   calcining said applied mixture to form a protective coating on said second side of said protective layer;
   wherein said protective coating has a thickness of greater than about 200 $\mu$m.

17. A method for making a sensor, comprising:
   disposing an electrolyte between a first side of sensing electrode and a first side of reference electrode, wherein said sensing electrode has a first electrical lead in electrical communication with said sensing electrode, and wherein said reference electrode has a second electrical lead in electrical communication with said reference electrode;

disposing a first side of a protective layer adjacent to a second side of said sensing electrode;

applying a mixture of a solvent, a fugitive material, and a first material to a second side of said protective layer, wherein said first material consists essentially of about 25 wt. % to about 75 wt. % gamma alumina, about 25 wt. % to about 75 wt. % alpha alumina, and up to about 5 wt % aluminum nitrate; and calcining said applied mixture to form a protective coating on said second side of said protective layer.

18. The method of claim 17, wherein said fugitive material is selected from the group consisting of carbon black, graphite, non-dissolved organics and combinations comprising at least one of the foregoing materials.

19. The method of claim 17, wherein said first material consists essentially of about 43.5 wt. % to about 54.5 wt. % gamma alumina, about 43.5 wt. % to about 54.5 wt. % alpha alumina, and about 1 wt. % to about 3 wt. % of aluminum nitrate.

20. The method of claim 17, wherein said protective coating has a thickness of greater than about 120 $\mu$m.

21. The method of claim 20, wherein said protective coating has a thickness of about 120 to about 160 micrometers.

22. The method of claim 17, wherein said first material consists essentially of about 25 wt. % to about 75 wt. % gamma alumina, about 25 wt. % to about 75 wt. % alpha alumina, and about 1 wt. % to about 5 wt % aluminum nitrate.

* * * * *